United States Patent [19]

Kranvogel

[11] Patent Number: 4,775,994
[45] Date of Patent: Oct. 4, 1988

[54] MOBILE X-RAY EXAMINATION UNIT

[75] Inventor: Feliks Kranvogel, Neunkirchen, Fed. Rep. of Germany

[73] Assignee: Siemens Aktiengesellschaft, Berlin and Munich, Fed. Rep. of Germany

[21] Appl. No.: 942,276

[22] Filed: Dec. 15, 1986

[30] Foreign Application Priority Data

Mar. 11, 1986 [DE] Fed. Rep. of Germany ....... 3608069

[51] Int. Cl.$^4$ .............................................. A61B 6/00
[52] U.S. Cl. ..................................... 378/197; 378/198
[58] Field of Search .............. 378/193, 194, 195, 196, 378/197, 198; 250/363 SC

[56] References Cited

U.S. PATENT DOCUMENTS 100,945 6/1936 Graves ................................. 378/198

FOREIGN PATENT DOCUMENTS

A0160749 11/1985 European Pat. Off. .
2405612 5/1979 France .
2337859 2/1975 Fed. Rep. of Germany ...... 378/195

Primary Examiner—Carolyn E. Fields
Assistant Examiner—Joseph A. Hynds
Attorney, Agent, or Firm—Hill, Van Santen, Steadman & Simpson

[57] ABSTRACT

The invention relates to a mobile X-ray examination unit including a C-bend which carries an X-radiator and a radiation receiver at its ends. The C-bend is displaceably seated on a carriage and hinged to the carriage, whereby the two articulation axes proceed parallel to one another. The arm has a fixed length, whereby this fixed length is dimensioned such and the arm is hinged to the carriage at such a location that the arm is pivotable, first, into a roughly vertical position and, second, into a roughly horizontal position and the C-bend is simultaneously pivotable into such a respective position that the X-radiator and the radiation receiver lie on a straight line proceeding about parallel to the arm.

2 Claims, 1 Drawing Sheet

MOBILE X-RAY EXAMINATION UNIT

BACKGROUND OF THE INVENTION

1. Field of the Invention

The invention relates to a mobile X-ray examination unit including a C-bend which carries an X-radiator and a radiation receiver at its ends, the C-bend being displaceably seated on a carriage and hinged to an arm at roughly its center, the other end of this arm being hinged to the carriage, whereby the two articulation axes proceed parallel to one another.

2. Description of the Prior Art

X-ray examination units of this type are used for the operating room. The C-bend must thereby be versatilely adjustable in space in order to be able to correspondingly adapt the radiation direction to the given conditions.

EP-A-O No. 160 749 discloses an X-ray examination unit of the type described. In order to achieve an adjustability of the radiation direction which meets the demands, the arm to which the C-bend is hinged is extensible in telescoping fashion, whereby the mechanism for adjusting the radiation direction is complicated and, accordingly, expensive and susceptible to disruption.

SUMMARY OF THE INVENTION

An object of the invention is to provide an X-ray examination unit of the type described above such that a universal adjustment of the radiation direction in space is possible with the assistance of a simple mechanism.

This object is achieved in accord with the invention in that the arm has a fixed length, whereby this fixed length is dimensioned such and the arm is hinged to the carriage at such a point that the arm can be pivoted, first into an approximately vertical position and, second, into an approximately horizontal position and the C-bend is simultaneously pivotable into such a respective position that the X-radiator and the radiation receiver lie on a straight line approximately parallel to the arm. In the X-ray examination unit of the invention, thus, a universal adjustability of the C-bend is possible with the assistance of a single arm of fixed length permitting elimination of adjustable columns, sleeves and the like and, in particular, permitting elimination of an arm extensible in telescoping fashion.

An especially practical embodiment results when the cables for the X-radiator and the radiation receiver are conducted in the C-bend and in the arm. In this construction, cables conducted to the X-radiator and to the radiation receiver in th open are eliminated. The cables lie covered in the arm and in the C-bend.

BRIEF DESCRIPTION OF THE DRAWINGS

The invention shall be set forth in greater detail below with reference to an exemplary embodiment shown in the drawing. Thereby shown are.

DESCRIPTION OF THE PREFERRED EMBODIMENTS

Figure 1:
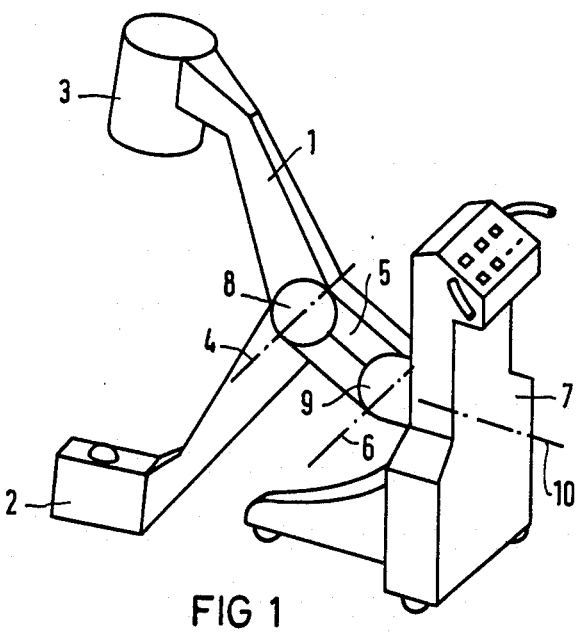
FIG. 1 is a perspective view of an X-ray examination unit of the invention.
Figure 2:
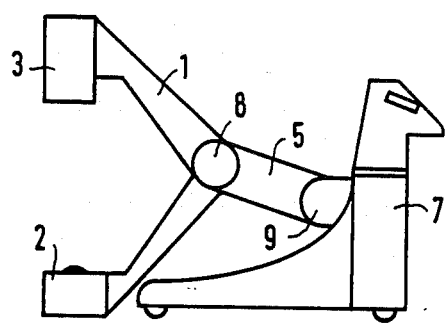
FIGS. 2-5 are side elevational views of various positions of the X-ray examination unit of FIG. 1.
Figure 3:
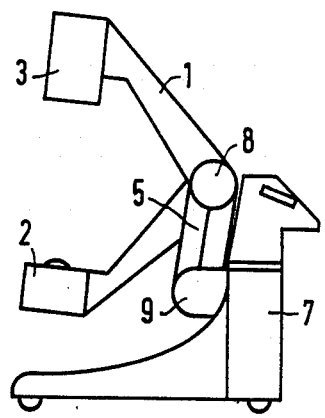
Figure 4:
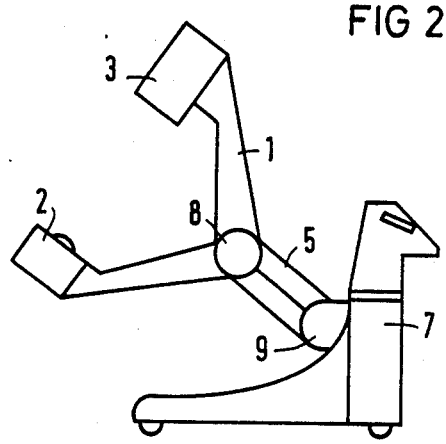
Figure 5:
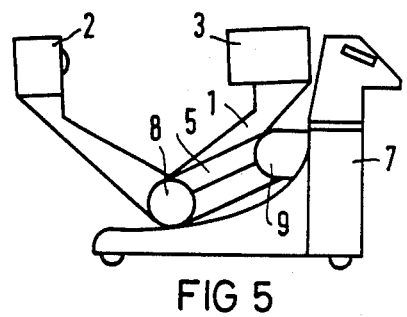

FIG. 1 shows an X-ray examination unit comprising a C-bend 1 at whose ends an X-radiator 2 and an X-ray image intensifier 3 are arranged. The C-bend can thus be brought up to a patient support such that it embraces the latter. The C-bend is connected to an arm 5 of fixed length so as to be pivotable around a horizontal axis 4, the other end of this arm 5 being hinged to a carriage 7 pivotable around a horizontal axis 6 that is parallel to the axis 4. The carriage 7 can be moved on the floor. The pivoting of the arm 5 relative to the carriage 7 around the axis 6 and the pivoting of the C-bend 1 (seated in about its center) relative to the arm 5 around the axis 4 ensues by means of electric motors 8, 9.

FIGS. 2 through 5 show various spatial attitudes of the C-bend 1. It follows from FIGS. 2 through 5 that the beam path in space can be set as desired. This is possible despite the fixed length of the arm 5 because, as may be particularly seen from FIGS. 3 and 5, the length of the arm 5 and the position of the articulation at the carriage 7 are selected such, taking the shape of the carriage 7 into consideration, that the arm 5 is pivotable into both a roughly vertical position (FIG. 3) as well as a roughly horizontal position (FIG. 5) ad the C-bend 1 is simultaneously pivotable into such a position that the X-radiator 2 and the radiation receiver 3 lie on a straight line approximately parallel to the arm 5. Oblique transilluminations of the patient are also possible since the arm 5 is connected to the carriage 7 pivotable around an axis 10 which is perpendicular to the axis 6 and likewise proceeds horizontally.

The cables of the X-radiator 2 and to the X-ray image intensifier 3 are conducted out of view inside the C-bend 1 and inside the arm 5.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A mobile X-ray examination unit including a C-bend which carries an X-radiator at one end and a radiation receiver at an opposite end, is displaceably seated on a carriage and hinged to a first end of an arm at roughly its center forming a first articulation axis, a second end of this arm being hinged directly to said carriage forming a second articulation axis, wherein the two articulation axes are parallel to one another, comprising the improvement wherein said X-ray examination unit is freely movable in a horizontal plane and said arm has a fixed length, said fixed length being dimensioned such and said arm being hinged to said carriage at such a location that said arm is pivotable, first, into a roughly vertical position and, second, into a roughly horizontal position and said C-bend being simultaneously pivotable into such a respective position that said X-radiator and said radiation receiver lie on a straight line approximately parallel to said arm.

2. A mobile X-ray examination unit comprising:
   a C-bend carrying an X-radiator at one end and a radiation receiver at an opposite end;
   a carriage freely movable in a horizontal plane;
   an arm pivotally connected at a first end to said C-bend, approximately at the center of said C-bend, to form a first articulation axis;

said arm being pivotally connected directly to said carriage at a second end to form a second articulation axis;
said two articulation axes being parallel to one another;
said arm having a fixed length and being dimensioned such and pivotally connected to said carriage at such a location that said arm is pivotable, first into an approximately vertical position, and second, into an approximately horizontal position;
said C-bend being simultaneously pivotable into a respective approximately horizontal and vertical position such that said X-radiator and said radiation receiver lie on a straight line approximately parallel to said arm.

* * * * *